(12) United States Patent
Towler et al.

(10) Patent No.: US 7,981,972 B2
(45) Date of Patent: Jul. 19, 2011

(54) SYNTHETIC GRAFT HAVING A GLASS NETWORK

(75) Inventors: Mark Robert Towler, County Clare (IE); Daniel Boyd, County Cork (IE)

(73) Assignee: University of Limerick, Limerick (IE)

( * ) Notice: Subject to any disclaimer, the term of this patent is extended or adjusted under 35 U.S.C. 154(b) by 661 days.

(21) Appl. No.: 11/990,336

(22) PCT Filed: Jul. 31, 2006

(86) PCT No.: PCT/IE2006/000080
§ 371 (c)(1),
(2), (4) Date: Feb. 12, 2008

(87) PCT Pub. No.: WO2007/020613
PCT Pub. Date: Feb. 22, 2007

(65) Prior Publication Data
US 2009/0093571 A1   Apr. 9, 2009

(30) Foreign Application Priority Data
Aug. 12, 2005   (IE) ..................................... 2005/0533

(51) Int. Cl.
C08F 8/42 (2006.01)
A61K 6/08 (2006.01)
(52) U.S. Cl. .......... 525/370; 525/221; 522/150; 522/81; 523/116
(58) Field of Classification Search ................. 525/221, 525/342, 370, 703; 522/150, 81; 523/116
See application file for complete search history.

(56) References Cited

U.S. PATENT DOCUMENTS

| | | | | |
|---|---|---|---|---|
| 5,130,347 A | * | 7/1992 | Mitra | 522/149 |
| 2006/0172877 A1 | * | 8/2006 | Fechner et al. | 501/48 |

FOREIGN PATENT DOCUMENTS

| | | |
|---|---|---|
| DE | 19530470 | 2/1997 |
| DE | 19832965 | 2/2000 |
| EP | 0323120 | 7/1989 |
| EP | 0386525 | 9/1990 |
| GB | 2264711 | 9/1993 |
| GB | 2310663 | 9/1997 |
| WO | 03028670 | 4/2003 |

OTHER PUBLICATIONS

International Search Report date Nov. 30, 2006.
Towler, et al.; "A preliminary study of an aluminum-free glass polyalkenoate cement"; *Journal of Materials Science Letters*, Jul. 15, 2002; pp. 1123-1126; Kluwer Academic Publishers.

* cited by examiner

*Primary Examiner* — Ling-Siu Choi
(74) *Attorney, Agent, or Firm* — Jacobson Holman PLLC

(57) ABSTRACT

A synthetic graft has a glass composition comprises silicon as a network former and Sr as a stable isotope acting as a network modifier. The composition contains calcium as a network modifier and Zn acting as a as either a network modifier or as a network former. The glass composition may be mixed with a solution of polyalkenoic acid to provide advantageous glass polyalkenoate cements (GPCs). These cements are particularly effective for use as bone cements and fillers in the human skeleton as they set at room temperature, have similar strengths to bone, chemically bond to both bone and surgical metal, and release therapeutic ions, which can assist in wound healing and bone re-growth.

8 Claims, 6 Drawing Sheets

Sr$^{2+}$ acting as a network modifier in a silicate glass.

Zn acting as a network former through the chanrge balancing of ZnO$_4$ tetrahedra by Sr$^{2+}$.

Zn$^{2+}$ acting as a network modifier in a silicate glass.

Illustrates the biaxial flexural strength of GPCs derived from glasses BT100-102.

Illustrates the compressive strength of GPCs derived from glasses BT100-102.

SYNTHETIC GRAFT HAVING A GLASS NETWORK

This is a national stage of PCT/IE06/000080 filed Jul. 31, 2006 and published in English.

INTRODUCTION

1. Field of the Invention

The invention relates to synthetic grafts having glass networks, either in granular form or as a cement.

2. Prior Art Discussion

At present it is known to provide synthetic bone cements for a variety of uses such as for hip replacements.

In the 1980's it was proposed to use Al-bases cements due to their success with dental work. However internal use closer to the nervous system gave rise to problems, including in extreme cases, renal failure.

Self-polymerizing poly methyl methacrylate ("PMMA") bone cement is the main material currently used for anchoring cemented diarthrodal joint prostheses to contiguous bone. It is accepted that such cements contribute significantly to aseptic loosening of prostheses, and have been implicated as one of the main causes of revision surgeries. These cements are beset with numerous drawbacks including: thermal and chemical necrosis of healthy bone stock, shrinkage during polymerization, stiffness mis-match between PMMA and bone leading to stress shielding, and 'weak-link' zones in the construct (at the implant-PMMA and the PMMA-bone interfaces), and invoking an inflammatory tissue response when cement particles interact with surrounding tissues These limitations retard the success of PMMA in arthroplastic procedures and inhibit further applications for which PMMA might be employed. For example, PMMA has restricted use in vertebroplasty (back surgery) due to concerns over thermal necrosis causing nerve damage.

Synthetic bone cements can also be based on calcium phosphates which have excellent bioactivity. However, they are too weak for most load-bearing applications, and are contraindicated in patients suffering from metabolic bone diseases as well as those suffering from acute traumatic injuries with open wounds that are likely to become infected.

Towler, M. R. et al, "A preliminary study of an aluminium-free glass polyalkenoate cement", Journal of Materials Science Letters, Jul. 15, 2002, pp 1123-1126 describes GPCs formed by the reaction of an ion leachable alumino-silicate glass with an aqueous solution of polyalkenoic acid.

Apparently because of these limitations, today only a small percentage of bone fillers used are synthetic materials. The only truly successful bone replacement material is bone itself, harvested either as auto-grafts (bone donated from the same patient) or allo-grafts (bone donated from another patient).

The invention is therefore directed towards providing an improved

SUMMARY OF THE INVENTION

According to the invention, there is provided a synthetic graft comprising a glass network comprising a silicate-based network former and a network modifier, wherein
the network modifier comprises strontium, and
the graft further comprises zinc as either a network former or a network modifier.

In one embodiment, the strontium is in the form of a stable isotope.

In one embodiment, the strontium is present as an $Sr^{2+}$ isotope.

In one embodiment, the $Sr^{2+}$ isotope performs charge balancing of a $ZnO_4$ tetrahedra In one embodiment, the zinc is present in the form $Zn^{2+}$.

In one embodiment, the glass network former comprises $SiO_2$ and ZnO.

In one embodiment, the glass network comprises calcium as an additional network modifier.

In one embodiment, calcium is present in the form $Ca^{2+}$.

In one embodiment, the glass network connectivity is in the range of 1 to 3.

In one embodiment, the glass network comprises SiO2 at a proportion in the range of 0.25 to 0.75 mole fraction and a corresponding proportion of any variation of Ca/Sr/Zn in the range of 0.75 to 0.25 mole fraction.

In one embodiment, the glass network comprises CaO—SrO—ZnO—$SiO_2$.

In one embodiment, the glass network comprises (0.05-X) CaO (X)SrO 0.42 $SiO_2$ 0.53 ZnO.

In one embodiment, the graft is in the form of a cement, comprising an acid and water in which the glass is mixed.

In one embodiment, the acid is polyalkenoic acid, the cement being a glass polyalkenoate cement.

In one embodiment, the concentration of acid is in the range of 20 wt % to 60 wt %, and most preferably in the range of 40 wt % to 50 wt %.

DETAILED DESCRIPTION OF THE INVENTION

Brief Description of the Drawings

The invention will be more clearly understood from the following description of some embodiments thereof, given by way of example only with reference to the accompanying drawings in which:—

FIG. 9 is an image of the surface of a cement of the invention after incubation at 37° for 1 day, while

DESCRIPTION OF THE EMBODIMENTS

Figure 1:
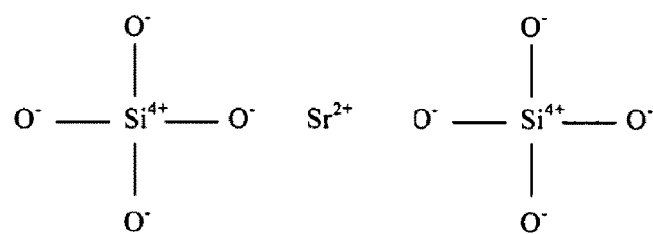
FIG. 1 is a diagram illustrating $Sr^{2+}$ acting as a network modifier in a silicate glass.

A glass composition comprises silicon as a network former and Sr as a stable isotope acting as a network modifier. Furthermore the composition contains calcium as a network modifier and Zn acting as a as either a network modifier or as a network former. The glass composition may be mixed with a solution of polyalkenoic acid to provide advantageous glass polyalkenoate cements (GPCs). These cements are particularly effective for use as bone cements and fillers in the human skeleton as they:
set at room temperature,
have similar strengths to bone, chemically bond to both bone and surgical metal, and release therapeutic ions, which can assist in wound healing and bone re-growth.

The beneficial effects of low doses of stable strontium in the treatment of osteoporosis was reported almost half a century ago, and more recent studies have pointed to effects such as inhibiting bone resorption by osteoclasts and promoting osteoblast replication and bone formation. Also, therapeutic effects have been noted for zinc (Zn). Zn is the second most prevalent trace element in the human body, with its highest concentrations being found in bone, indicating how important Zn is to healthy bone growth and development. The literature indicates that the introduction of zinc into bone in controlled amounts results in increased alkaline phosphatase activity in osteoblasts, and increased DNA in osteoblasts, which positively affects the collagen and calcium content of bone. As a result of this increased activity, both the compressive and flexural strength of bone are dramatically improved. It is also the case that bone growth retardation is a common finding in various conditions associated with zinc deficiency. Zinc has also been linked with the action of over 300 enzymes involved in many different metabolic processes and is also linked with the structure, synthesis and degradation of DNA. It therefore plays an crucial role in cell replication.

Therefore the combined release of Sr and Zn from GPCs derived from aluminium free $SrO$—$CaO$—$ZnO$—$SiO_2$ glasses is likely to be extremely beneficial for patients undergoing orthopaedic procedures where such GPCs may be used.

In one example the glass composition is (0.05-X)CaO (X)SrO 0.42 $SiO_2$ 0.53 ZnO. However, in other examples CaO is incrementally replaced with SrO and the composition can be based on any variation of $CaO$—$SrO$—$ZnO$—$SiO_2$ such that the network connectivity of the glass is maintained between 1 and 3.5. In all cases Sr and Zn are present, with Sr acting as a network modifier and the Zn acting as either a network modifier or former.

Mixing glass powder with the correct amount of polyalkenoic acid (usually polyacrylic acid), and water produces a GPC. The GPCs produced from such glasses as described herein have clinically acceptable handling properties and strengths for hard tissues applications and are antibacterial and bioactive in nature.

In terms of the glass chemistry, because $Sr^{2+}$ and $Ca^{2+}$ have similar ionic radii, they also share similar roles in the glass structure. They are network modifiers, capable of disrupting the network, making the glass suitable for GPC formation.

Figure 2:
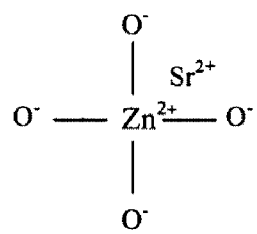
FIG. 2 is a diagram illustrating charge balancing of $ZnO_4$ tetrahedra by $Sr^{2+}$.
Figure 3:
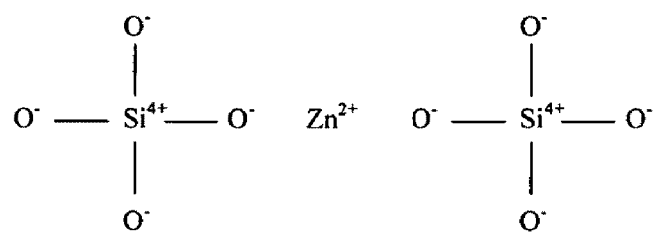
FIG. 3 illustrates $Zn^{2+}$ acting as a network modifier in a silicate glass.

FIG. 1 illustrates the network modifying role of $Sr^{2+}$ in a silicate network, FIG. 2 shows Zn acting as a network former, and FIG. 3 shows $Zn^{2+}$ acting as a network modifier in a silicate glass.

Further to $Sr^{2+}$ playing a network modifying role, in the $CaO$—$ZnO$—$SiO_2$ glass networks, the inclusion of $Sr^{2+}$ may also facilitate the stabilisation of $ZnO_4$ tetrahedra in the glass, as illustrated in FIG. 2. Usually $Zn^{2+}$ acts as a network modifier but can act as a network former in the glass similarly to $SiO_2$ provided there are charge balancing cations available in the glass network.

Two Sr containing glasses were considered and are represented in Table 1. They represent a half substitution (Glass F) and a fall substitution (Glass G) of calcium for the calcium zinc silicate glass termed 'Glass E'.

TABLE 1

$SrO$—$CaO$—$ZnO$—$SiO_2$ Glass Compositions (mole fractions).

| Glass | SrO | CaO | ZnO | $SiO_2$ |
|---|---|---|---|---|
| E | 0 | 0.05 | 0.53 | 0.42 |
| F | 0.025 | 0.025 | 0.53 | 0.42 |
| G | 0.05 | 0 | 0.53 | 0.42 |

When mixed with polyacrylic acid (PAA) and water these glasses form glass polyalkenoate cements (GPCs) whose setting times can be tailored to be clinically acceptable in terms of ISO9917 and ISO5833 (150-900 seconds). The strengths of the cements examined can also be tailored from 5 MPa to 65 MPa in compression, and 5 MPa to 50 MPa under biaxial flexure.

Figure 4:
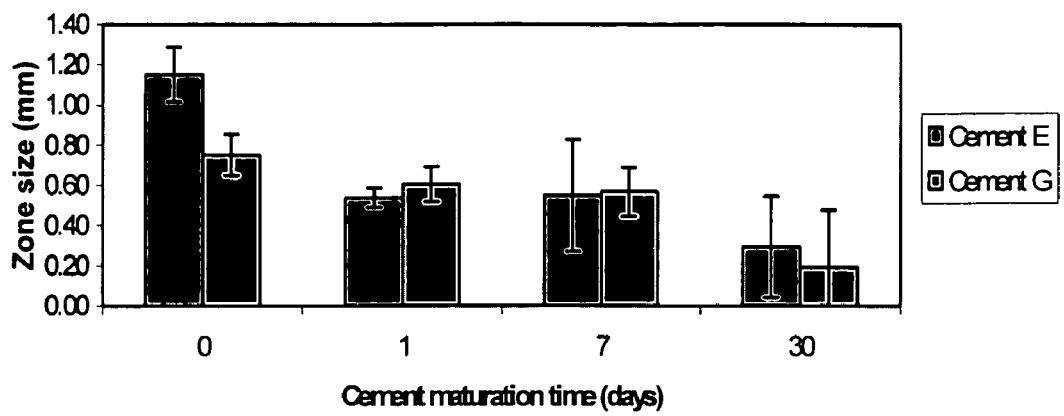
FIGS. 4 and 5 are plots illustrating cement maturation times.
Figure 5:
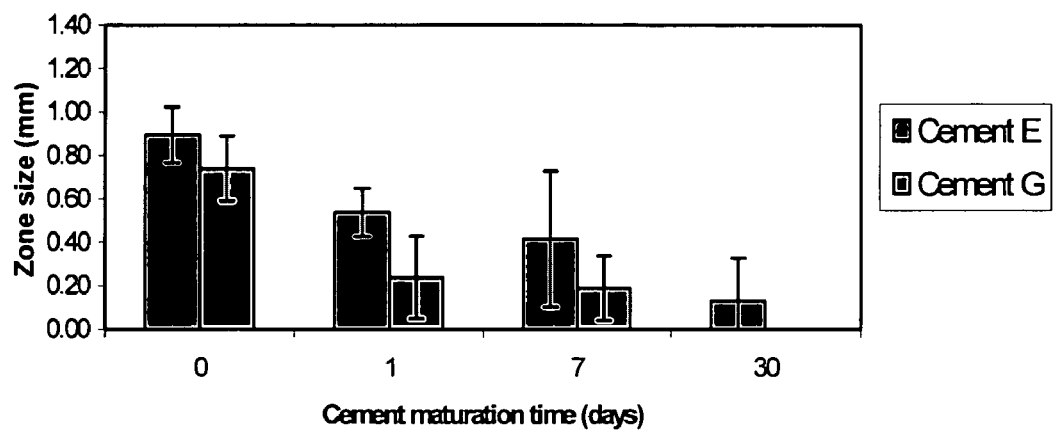

The resultant cements are also suitably radiopaque to meet the requirements of ISO4049 and can therefore be monitored for stability in the long term. Maturation time results are illustrated in FIGS. 4 and 5.

The cements formed from Sr glasses were also shown to be antibacterial in nature against *Streptococcus mutans* and *Actinomyces viscosus*; bacteria commonly associated with postoperative skeletal infection. Zones of inhibition up to 1.4 mm around cement samples where detected, indicating that $SrO$—$ZnO$—$CaO$—$SiO_2$ based GPC will inhibit the proliferation of bacteria and decrease the incidence of postoperative infection, Studies have outlined the complications associated with bacterial infection after total hip arthroplasty (THA). The bacteria most commonly found in infected hip joints are *Streptococci* and *Staphylococci*, though members of numerous other genera such as *Actinomyces*, including *Actinomyces viscosus, Prevotella* and *Pseudomonas* have also been reported. Thus, the two bacteria considered herein are representative of the many bacterial species isolated from infected hip joints. The growth inhibitory effects observed with *S. mutans* and *A. viscosus* in this work are therefore clearly of relevance to prevention of THA infections in a clinical setting.

Bacterial infections of prosthetic hip joints have a considerable financial consequence, both for the patient and the healthcare provider, and can necessitate extended antibiotic treatment and numerous surgical interventions, as well as causing long-term physical and mental hardship for the patient. In an attempt to avoid such infections, antibiotic-impregnated cement spacers have been utilised in THA in order to achieve localised, extremely high concentrations of antibiotics that minimise bacterial growth. Problems associated with such antibiotic-impregnated cements, however, include weakening of the cement itself and the generation of antibiotic-resistant bacteria in infected implant sites.

As zinc inhibits multiple activities in the bacterial cell, such as glycolysis, transmembrane proton translocation and acid tolerance, it has been shown to exhibit an antibacterial effect at considerably lower concentrations than many antimicrobial agents. Furthermore, though generally regarded as bacteriostatic, it can have bactericidal effects also, particularly when used in combination with other ions, such as fluorine or other antibacterial agents like Strontium. Therefore, the use of strontium/zinc-containing cements such as those described here might permit incorporation of antibiotics at considerably lower concentrations than are currently necessary to avoid bacterial infections in THA. This would not only reduce sample weakening but, due to the simultaneous presence of the two antibacterial agents, might be expected to reduce the rate at which antibiotic resistant bacteria arise.

The range of strontium and zinc permitted in the glass is very broad, however provided that the NC does not decrease below 1 (0.25 mole fraction of the glass is $SiO_2$) the remaining 0.75 mole fraction of the glass can comprise any variation of Ca/Sr/Zn. At the other end of the range there may be up to 0.75 mole fraction of SiO2 and corresponding mole fraction of Ca/Sr/Zn of 0.25

The increases in strengths of the cements of the invention are shown in Table 2 below.

TABLE 2

Comparison of the flexural strengths (Standard deviations in parenthesis) of cements formed from Glasses E, F and G.

| Cement | 1 Day (MPa) | 7 Days (MPa) | 30 Days (MPa) | 90 Days (MPa) |
|---|---|---|---|---|
| EE7 50 wt % | 5 (1) | 7 (1) | 10 (1) | 10 (2) |
| EE9 50 wt % | 27 (2) | 25 (5) | 32 (3) | 31 (5) |
| FE7 50 wt % | 9 (3) | 10 (1) | 11 (1) | 10 (1) |
| FE9 50 wt % | 48 (8) | 48 (4) | 50 (2) | 39 (2) |
| GE7 50 wt % | 11 (2) | 12 (1) | 13 (2) | 15 (2) |
| GE9 50 wt % | 48 (4) | 49 (2) | 48 (6) | 40 (6) |

It is preferable that the glass has a network connectivity of between 1.2 and 3.2, although Sr can be added in higher doses.

EXAMPLES

Consider the two glass compositions described in Table 3.

TABLE 3

Glass formulations expressed as mole fractions

| Glass | CaO | SrO | $SiO_2$ | ZnO |
|---|---|---|---|---|
| A | 0.05 | 0 | 0.42 | 0.53 |
| B | 0 | 0.05 | 0.42 | 0.53 |

Glass A contains calcium, zinc and silica, while in glass B the calcium was replaced by strontium. Appropriate amounts of analytical grade silica, zinc oxide and either calcium carbonate or strontium carbonate were weighed out in a plastic tub and mixed in a ball mill (1 h), followed by drying in a vacuum oven (100° C., 1 h). The pre-fired glass batch was transferred to a mullite crucible for firing (1580° C., 1 h). The glass melts were then shock quenched into demineralised water and the resulting frit was dried, ground and sieved. The glass that passed through a 45 μm sieve was used to produce the cements.

Polyacrylic acid ("PAA") was supplied in aqueous solution (25% w/v) by Ciba speciality polymers (Bradford, UK). The acid was coded E7 and had an average molar mass ($M_n$) of 8,140. The acid was freeze-dried, ground and sieved through a <90 μm filter.

Two cement formulations were prepared, A and B, based on glasses A and B above, respectively. Each formulation used 1 g of the corresponding glass, 0.36 g of PAA and 0.55 ml of water, resulting in a P:L ratio of 1:0.91 for both cements. Split ring moulds were used to produce cement discs (n=3) with a thickness of 1 mm and an internal diameter of 5 mm. The cements were mixed on a clean glass slab with a stainless steel dental spatula. Thirty seconds after mixing the moulds were filled to excess with cement, covered with acetate and clamped between Perspex plates. The clamped samples were maintained at 37° C. for 1 h after the start of mixing. Flash was subsequently removed by grinding samples in their moulds with 1200 grit silicon carbide paper. Samples were de-moulded, washed with ethanol and stored in 10 ml aliquots of distilled water. Cement discs were removed from the water after 30 min, 1 h, 2 h, 4 h, 24 h, 7 days and 30 days. The zinc concentration of the extracts was measured using a Varian SpectrAA-400 Atomic Absorption Spectrometer, with a lamp-current of 5 mA in an air/acetylene flame with wavelength 213.9 nm. Standard solutions of 0.5 ppm, 1.0 ppm, 1.5 ppm and 2.0 ppm were used to calibrate the system prior to use and three measurements were taken from each aliquot in order to determine the mean concentration of zinc at each time interval.

For preparation of a cement implanted bone sample a piece of bovine femur (5 cm×5 cm×2.5 cm) was cleaned and a hole (5 mm Ø) was drilled through the center of the bone, followed by thorough washing with distilled water. Cement A was mixed as described previously and used to fill the hole in the bone to excess. This was covered at either end with acetate sheets, clamped between two steel plates and allowed to set for 1 h at 37° C. The construct was then removed from the clamp and each surface polished gently using 1200 grit silicon carbide paper. The construct was stored in distilled water for 30 days, following which it was removed, dried and lightly polished.

A JOEL JSM-840 scanning electron microscope (SEM) equipped with a Princeton Gamma Tech (PGT) energy dispersive X-ray (EDX) system was used to obtain secondary electron images and to carry out chemical analysis of the bone-cement interface. EDX measurements were performed across the bone-cement interface in order to examine the extent of ion migration into the bone. Zinc and calcium measurements were taken at sites ranged from 60 μm on the bone side of the bone-cement interface, through the interface, to 60 μm into the cement, with samples taken 20 μm distances apart. All EDX spectra were collected at 20 kV, using a beam current of 0.26 nA. Quantitative EDX converted the collected spectra into concentration data by using standard reference spectra obtained from pure elements under similar operating parameters, according to standard procedures.

Agar Disc-Diffusion Test

The antibacterial activity of the cements was evaluated against the oral bacterial species *S. mutans* (American Type Culture Collection, ATCC, 25175) and *A. viscosus* (ATCC 19246), using the agar disc-diffusion method. The bacteria were grown from stock cultures on brain heart infusion (BHI) agar at 37° C. for 16 h and isolated colonies were used to seed fresh cultures in 10 ml Luria Broth (LB). After incubation at 37° C. for 12-16 h with shaking (200 rpm), the cultures were diluted in Mueller Hinton (MH) broth to give an $OD_{600}$ of 0.05 for *S. mutans* and 0.1 for *A. viscosus*. A 350-μl volume of each bacterial suspension was streaked using clinical swabs on MH agar plates containing agar of 4 mm height, following which 2-3 discs of each material were placed on the agar. The plates were inverted and incubated under aerobic conditions (36 h, 37° C.). Callipers were used to measure zones of inhibition at three different diameters for each disc and zone sizes were calculated as follows:

Size of inhibition zone(mm)=(haloØ−discØ)/2.

All cements were analysed in triplicate and mean zone sizes±standard deviations were calculated.

Zinc Release Measurements

Figure 6:
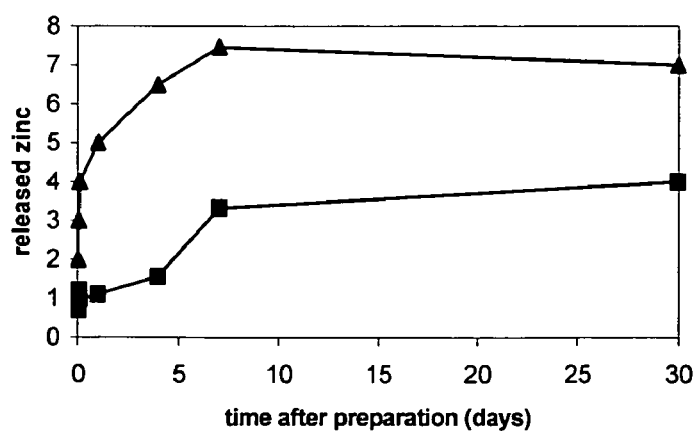
FIG. 6 is a plot of cumulative zinc release from two cements up to 30 days after synthesis.

Cumulative zinc release from each cement was measured at intervals up to 30 days. In both cements the rate of zinc release was seen to decrease with respect to time, with the highest release rates measured immediately after production and no detectable zinc being released after 7 days (FIG. 6).

The absolute levels of zinc released were lower in the case of cement B (square dots) than cement A (triangular dots), even though the glasses used as the base for the two cements contain identical amounts of zinc (Table 3). There is no obvious reason why this should be the case but it is possible that the replacement of calcium with strontium in glass B results in a more integral network, thereby inhibiting the release of zinc. Further investigation of the glass structure and the mechanical properties of the cements would be necessary to confirm this.

Investigation of Bone-Cement Interface

SEM and EDX were used to study the interface of the GPC implanted into bone and to generate calcium and zinc profiles across the interface. Control EDX data were measured for bone 2 cm from the bone-cement interface and at the centre of the implant for the cement. The EDX data indicated significant migration of zinc into the bone from a depth of 20-40 μm in the cement. This migration increased the normal zinc content in the bone from 3.1 wt %, as determined in the bone control sample, to 14.8 wt % 60 μm away from the cement interface in the bone. Given that zinc ions have been shown to have significant antibacterial effects in vivo and in vitro, this increased concentration of zinc ions in the cement-contiguous bone, and at the bone-cement interface in particular, may have important implications for the inhibition of growth of contaminating bacteria in prosthetic joints.

TABLE 4 below shows farther glass compositions.

| Glass code | SrO | CaO | ZnO | SiO$_2$ |
|---|---|---|---|---|
| BT100 | 0 | 0.16 | 0.36 | 0.48 |
| BT101 | 0.04 | 0.12 | 0.36 | 0.48 |
| BT102 | 0.08 | 0.08 | 0.36 | 0.48 |
| BT103 | 0.12 | 0.04 | 0.36 | 0.48 |

Cement Preparation from Table 4 Glasses

GPCs were produced using polyacrylic acid (coded E9 at UL) with a molecular weight of 80,800. GPCs were produced using a 2:1.5 powder liquid ratio, with concentration of acid equal to 40, 45 and 50 wt %. Cements were mixed on cleaned glass slabs and dental spatulas at 23° C.

Determination of Compressive Strength.

The compressive strengths of the cements were assessed in accordance with ISO9917. Spilt ring moulds (4 mm Ø, 6 mm height), were filled to excess with freshly mixed cement and then covered with acetate. The moulds were then sandwiched between 2 stainless steel plates, clamped, and incubated (37° C., 1 hour). Following incubation, the moulds were removed from the clamps. Flash around the moulds was removed using a grinding wheel (100 rpm) and 1200 grit silicon carbide paper. This ensured that all compression samples had flat ends, which were parallel to one another. Once ground, the samples were de-moulded, placed in distilled water and incubated (37° C.) for 1, 7, 30 or 90 days. After each time frame, wet compression samples were loaded on an Instron 4082 universal testing machine (Instron Ltd., High Wycombe, Bucks, U.K.) using a load cell of 5 kN at a crosshead speed of 1 mm·min$^{-1}$. Once removed from the storage water the samples were not dried, rather they were immediately placed on the test jig.

Five samples for each cement formulation and incubation time were tested.

Determination of Biaxial Flexural Strength:

The biaxial flexural strength of cements was determined using three support bearings on a test jig. Within 60 seconds after mixing of the cement, rubber moulds (Ø12 mm, 2 mm thick) were filled to excess with cement. The moulds were then sandwiched between two stainless steel plates, clamped, and incubated (37° C., 1 hour). Following incubation the samples were de-moulded and flash was removed from the edges of each disc using 1200 grit silicon-carbide paper. Samples were then placed in distilled water (13 ml) and incubated for 1, 7, 30 or 90 days. Sample thickness was measured using digital vernier callipers. The test jig was fixed to an Instron 4082 universal testing machine (Instron Ltd., High Wycombe, Bucks, U.K.) using a load cell of 1 kN at a crosshead speed of 1 mm·min$^{-1}$. Five samples for each cement formulation and incubation time were tested. Biaxial flexural strength (BFS was calculated according to Equation 1:

$$BFS = \frac{\rho(N)}{t^2}\{0.63\ln(r/t) + 1.156\} \quad \text{Equation 1}$$

Where:
ρ: Fracture load (N).
t: Sample thickness (mm).
r: Radius of the support diameter (mm).
Simulated Body Fluid (SBF) Trial:

Cement discs (n=3) were produced is the same way as those produced for the determination of biaxial flexural strength. Rubber moulds (Ø12 mm, 2 mm thick) were then filled to excess with cement. The moulds were then sandwiched between two acetate sheets attached to stainless steel plates; the assembly was then clamped, and incubated (37° C., 1 hour). Following incubation the samples were de-moulded and flash was removed from the edges of each disc using 1200 grit silicon-carbide paper. Samples were then placed in of SBF, for 1, 7, and 21 days; such that 1 m$^2$ of material was exposed to 25 ml SBF After aging, the materials were removed from the SBF, rinsed with purified water then placed on clean petri dishes and allowed to dry (37° C., 12 hours). Scanning electron microscopy (SEM), and quantitative energy dispersive x-ray analysis (Quantitative-EDX) were employed to performed surface analysis.

Figure 7:
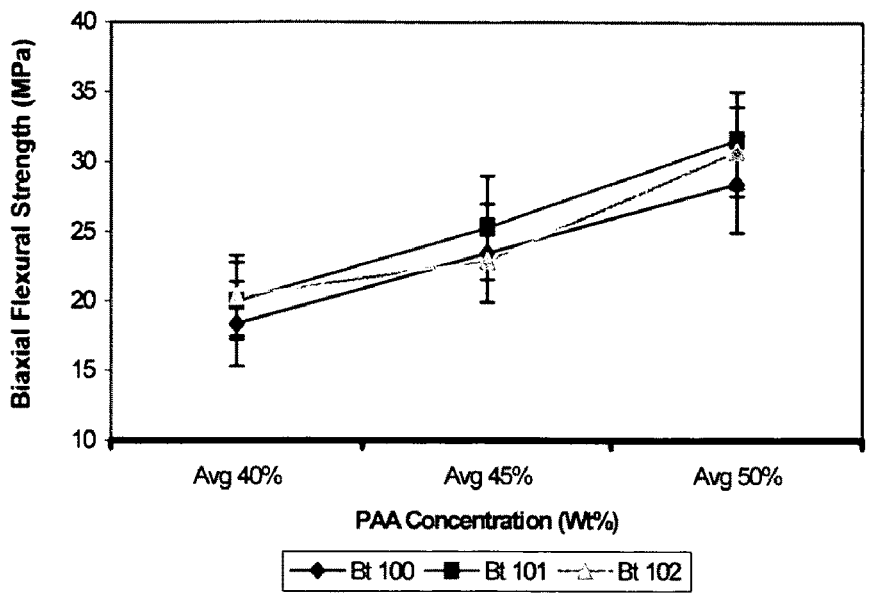
FIG. 7 is a plot illustrating biaxial flexural strength.
Figure 8:
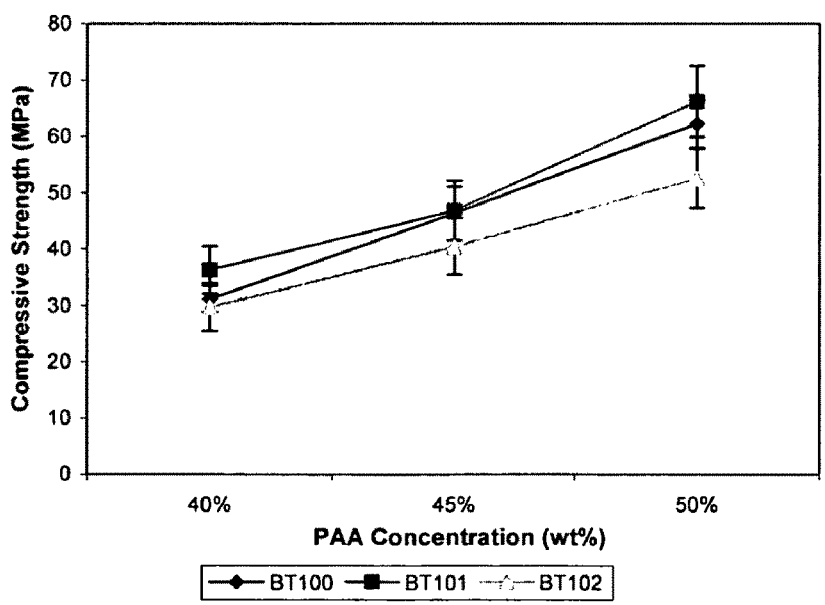
FIG. 8 is a plot illustrating compressive strength of cements of the invention.

The results are illustrated in the plots of FIGS. 7 and 8, in which FIG. 7 illustrates the biaxial flexural strength of GPCs derived from glasses BT100-10, and FIG. 8 illustrates the compressive strength of GPCs derived from glasses BT100-102

Figure 9:
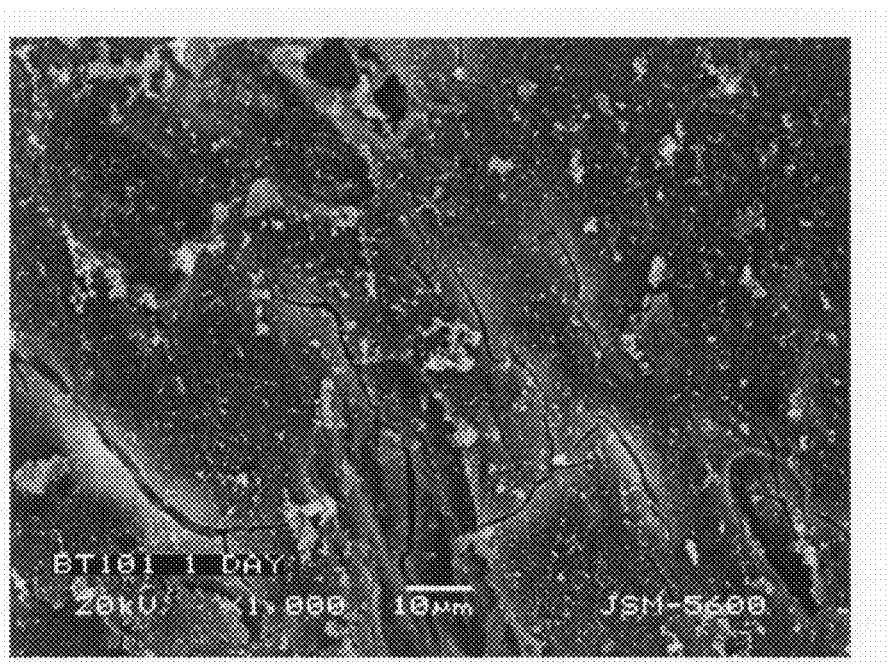
Figure 10:
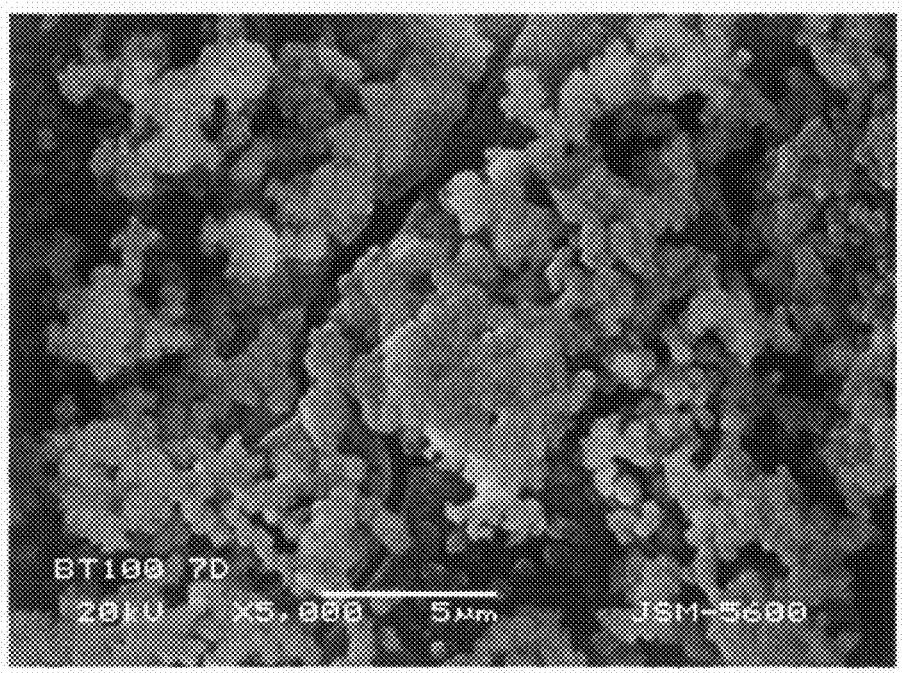
FIG. 10 shows that for 7 days.
Figure 11:
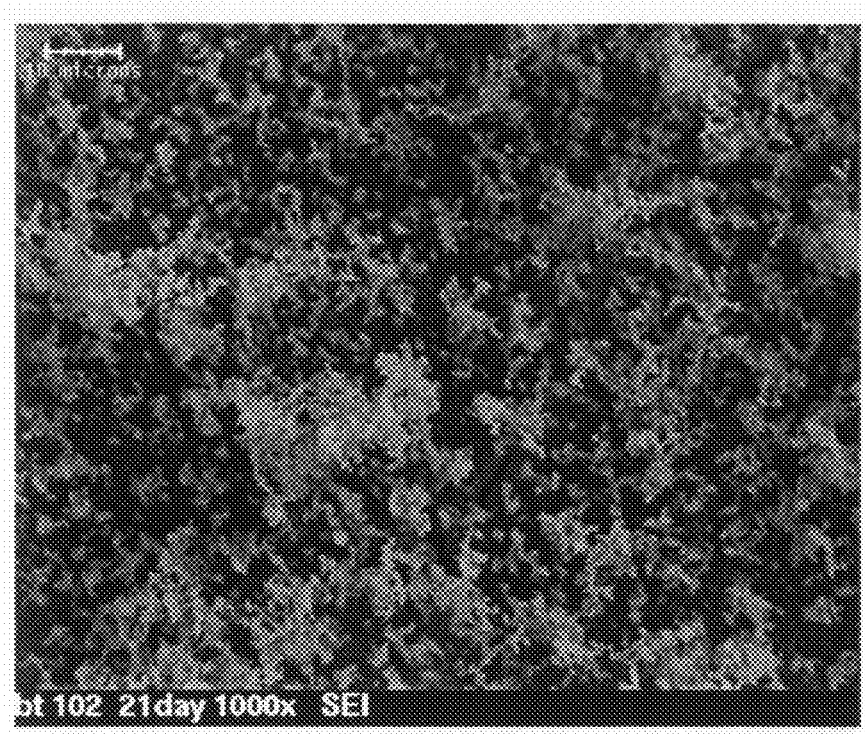
FIG. 11 shows that for 21 days.

FIGS. 9 to 11 illustrate a selection of results obtained from the SBF trial carried out on cements derived from glasses BT100, 101, 102. FIG. 9 shows the surface of Glass Polyalkenoate Cement derived from glass BT101 after incubation in SBF at 37° C. for 1 day (×1000). The clusters at the surface were identified as a Calcium phosphate precipitate. All cements produced exhibit such precipitates after 1 day. FIG. 10 shows surface of Glass Polyalkenoate Cement derived from glass BT100 after incubation in SBF at 37° C. for 7 days (×5000). The clusters at the surface were identified as a Calcium phosphate precipitate, which had increased in both density and coverage by 7 days (relative to 1 day samples). All cements produced exhibit such precipitates after 7 days. FIG. 11 shows the surface of Glass Polyalkenoate Cement derived from glass BT101 after incubation in SBF at 37° C. for 21 days (×1000). The clusters at the surface were identified as a Calcium phosphate precipitate, which had increased in both density and coverage by 21 days (relative to 1 and 7 day samples). All cements produced exhibit such precipitates after 21 days.

Figure 12:
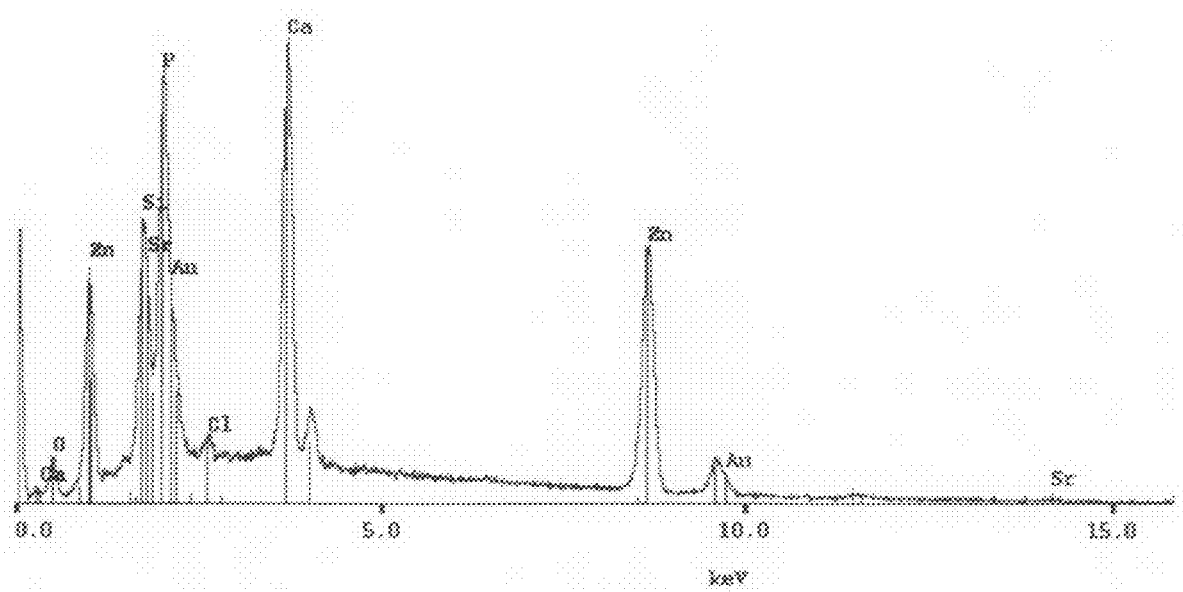
FIGS. 12, 13, and 14 are plots showing corresponding EDX results for the stages of FIGS. 9 to 11.
Figure 13:
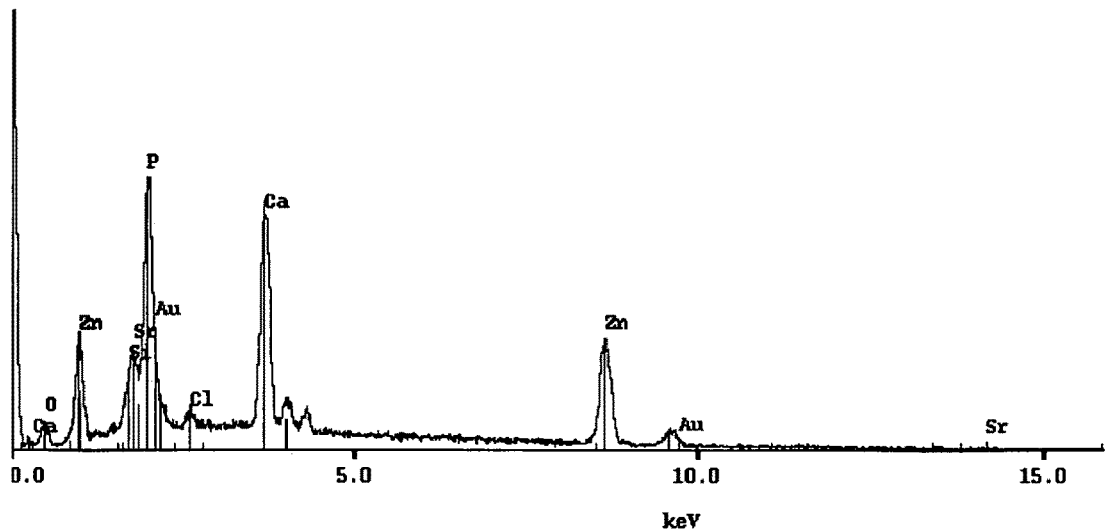
Figure 14:
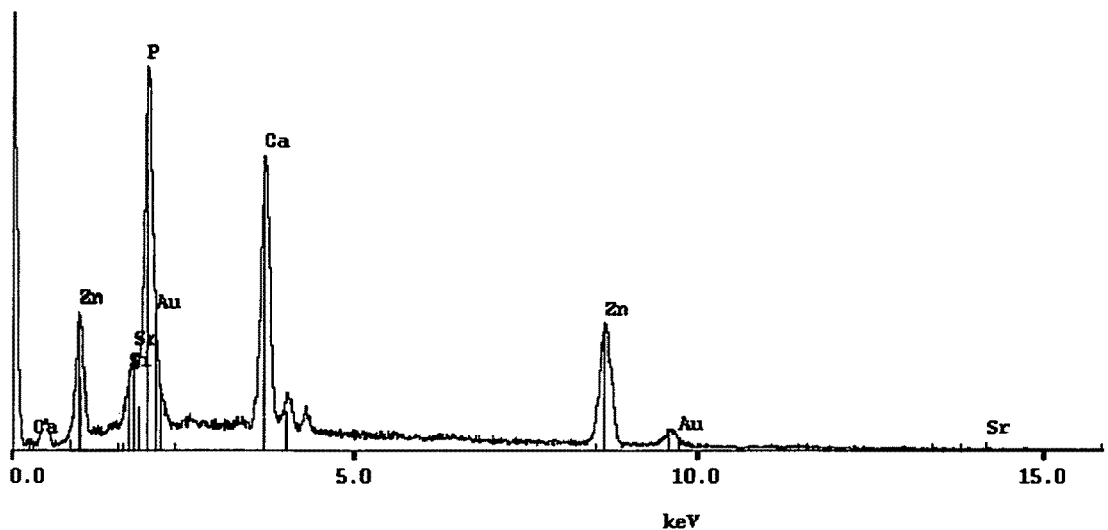

FIGS. 12 to 14 are the EDX results taken from the surfaces of Glass Polyalkenoate cements derived from glass BT101. These results, in conjunction with the SEM images, clearly indicate the presence of a bioactive calcium phosphate layer at the surface of the new materials. Again, for succinctness, only a representative number (three) of EDX patterns are shown, because each cement produced similar patterns. FIG. 12 shows EDX results for surface of BT101 after 1 day. The results clearly show a phosphorus peak attributable to the bioactive Calcium phosphate layer at the surface of the cements. FIG. 13 shows EDX results for surface of BT101 after 7 day. The results continue to show a phosphorus peak attributable to the bioactive Calcium phosphate layer at the surface of the cements. FIG. 14 shows EDX results for surface of BT101 after 21 days. The results continue to show a phosphorus peak attributable to the bioactive Calcium phosphate layer at the surface of the cements.

The ability of hard tissue biomaterials to bond to bone is regularly evaluated by examining the ability of apatite to form on its surface when placed in simulated body fluid. Simulated body fluid is a synthetic solution whose ionic concentrations are nearly equal to that of human blood plasma. It is the general consensus that the formation of such a layer is an essential precondition to support bone growth and bonding of the cement in vivo. The SEM images (FIG. 9-FIG. 11) indicate the formation of such a surface layer on the all-cement formulations examined after one day, which increases in both coverage and density up to twenty-one days. The spherical morphology of the precipitates, in conjunction with the EDX data (FIG. 12-FIG. 14), provides further confirmation that the surface layer precipitates calcium phosphates. Therefore it can be concluded that for cements examined each one will likely form a direct bone with bone when used in vivo.

The glasses, such as CaO—SrO—ZnO—$SiO_2$, may be used as synthetic bone grafts in isolation; that is to say without making a cement from them. Some typical applications of such granulated glass include repair of trauma defects, bony defects/acetabulu, femur, tibia etc, spinal stabilization, arthroplasty bone stock defects, long bone acute fractures, and as a graft extender. The glasses of the invention could be used in such applications, and they facilitate the therapeutic release Zn and Sr, which could see them advantageously exploited for use in patients with osteoporosis to treat locally areas affected by the metabolic bone disease.

The invention is not limited to the embodiments described but may be varied in construction and detail.

The invention claimed is:

1. A synthetic bone graft comprising a glass composition comprising a silicate-based network former and a network modifier, wherein the glass composition includes zinc as either a network former or a network modifier, strontium as a network modifier, and calcium as an additional network modifier; and the glass composition comprises $SiO_2$ at a proportion in the range of 0.25 to 0.75 mole fraction and a corresponding proportion of a variation of calcium, strontium, and zinc in the range 0.75 to 0.25 mole fraction, in which:

the strontium is present as SrO at a proportion in the range of 0.025 to 0.12 mole fraction;

the calcium is present as CaO at a proportion in the range of 0.04 and 0.16 mole fraction; and the zinc is present as ZnO at a proportion making up the balance of the mole fraction and wherein the glass composition has a network connectivity in the range of 1 to 3.5.

2. The synthetic bone graft as claimed in claim 1, wherein the strontium is in the form of a stable isotope.

3. The synthetic graft as claimed in claim 1, wherein the graft is in granular form.

4. A synthetic bone cement comprising a glass composition mixed in an acid and water, the glass composition comprising a silicate-based network former and a network modifier, wherein the glass composition includes zinc as either a network former or a network modifier, strontium as a network modifier, calcium as an additional network modifier;

and the glass composition comprises $SiO_2$ at a proportion in the range of 0.25 to 0.75 mole fraction and a corresponding proportion of any variation of calcium, strontium, and zinc in the range 0.75 to 0.25 mole fraction, in which:

the strontium is present as SrO at a proportion in the range of 0.025 to 0.12 mole fraction;

the calcium is present as CaO at a proportion in the range of 0.04 and 0.16 mole fraction;

the zinc is present as ZnO at a proportion making up the balance of the mole fraction;

and wherein the glass composition has a network connectivity in the range of 1 to 3.5.

5. The synthetic bone cement as claimed in claim 4, wherein the acid is a polyalkenoic acid.

6. The synthetic bone cement as claimed in claim 4, wherein the concentration of acid is in the range of 20 wt % to 60 wt %.

7. The synthetic bone cement as claimed in claim 4, wherein the concentration of acid is in the range is 40 wt % to 50 wt %.

8. The synthetic bone cement as claimed in claim 4, wherein the polyalkenoic acid is a polyacrylic acid.

* * * * *